(12) United States Patent
Ando et al.

(10) Patent No.: US 6,365,548 B1
(45) Date of Patent: Apr. 2, 2002

(54) TREATMENT METHOD FOR PRESERVING CUT FLOWERS

(75) Inventors: Toshio Ando, Matsudo; Takashi Kokubun, Chichibu; Tadashi Sekiyama, Kamakura, all of (JP)

(73) Assignee: Nikken Rentacom Co., Ltd., Tokyo (JP)

( * ) Notice: Subject to any disclaimer, the term of this patent is extended or adjusted under 35 U.S.C. 154(b) by 0 days.

(21) Appl. No.: 09/461,218

(22) Filed: Dec. 16, 1999

(30) Foreign Application Priority Data

| Dec. 28, 1998 | (JP) | 10-373860 |
| Jun. 14, 1999 | (JP) | 11-166428 |
| Jun. 15, 1999 | (JP) | 11-168686 |
| Nov. 2, 1999 | (JP) | 11-312780 |

(51) Int. Cl.⁷ .................................................. A01N 3/02
(52) U.S. Cl. ..................................................... 504/114
(58) Field of Search ......................................... 504/114

(56) References Cited

U.S. PATENT DOCUMENTS 5,252,537 A * 10/1993 De Winter-Scailteur .... 504/114

* cited by examiner

*Primary Examiner*—S. Mark Clardy
(74) *Attorney, Agent, or Firm*—Townsend & Banta

(57) ABSTRACT

The present invention is a treatment method for preserving cut flowers, which has a dehydration process for removing the tissue water of cut flowers using a solvent, and a permeation process for letting polyethylene glycol permeate after dehydration, to substitute the solvent by polyethylene glycol, characterized in that the dehydration process is effected while the cut flowers are fixed in a container having a proper amount of a molecular sieve spread over its bottom and filled with a solvent having a specific gravity smaller than that of water, wherein the specific gravity of the solvent is measured to monitor the change of the solvent in dehydratability, and the time when the specific gravity suddenly rises is detected as the time for exchanging the molecular sieve for a new one, to restore the dehydratability of the solvent, thereby allowing the solvent to be used continuously and allowing the dehydration process to be continued without waste of time.

Furthermore, if a washing process for washing the cut flowers containing polyethylene glycol as a substitute of the tissue water by a solvent not containing polyethylene glycol is added, the stickiness of the cut flowers otherwise caused after a drying process can be prevented.

24 Claims, 5 Drawing Sheets

F I G. 2
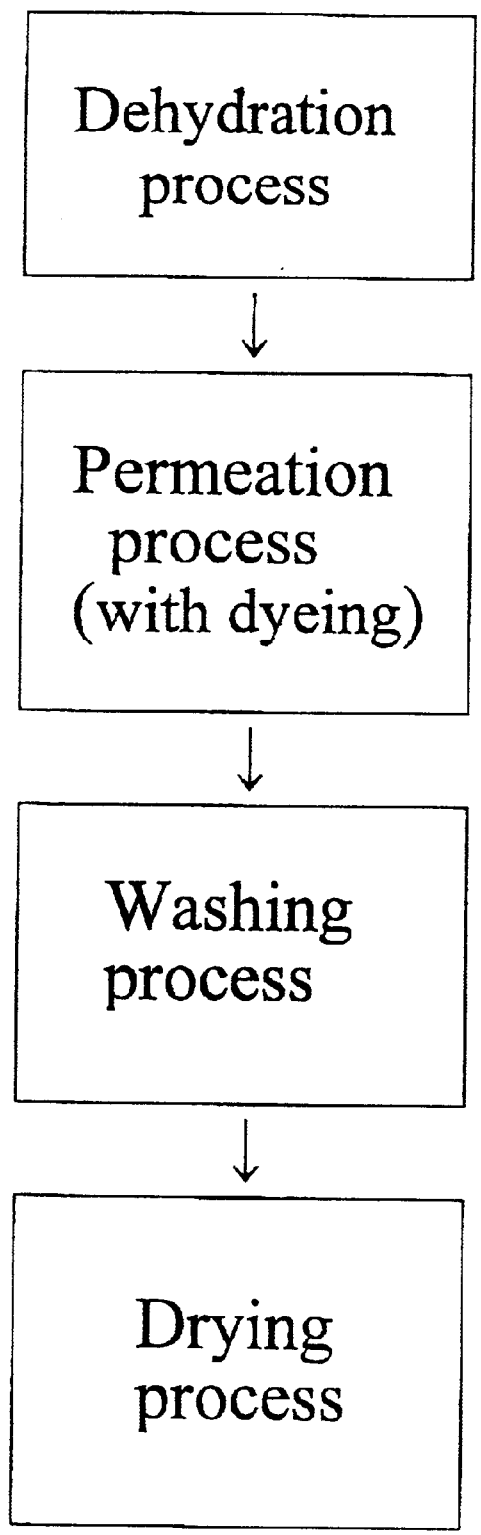

TREATMENT METHOD FOR PRESERVING CUT FLOWERS

FIELD OF THE INVENTION

The present invention relates to a treatment method for preserving cut flowers.

BACKGROUND OF THE INVENTION

Treatment methods for preserving cut flowers such as roses, to keep them appearing like natural flowers for a long period time for decoration are proposed, for example, in PCT International Publication No. WO91/03160 and U.S. Pat. No. 4,828,890, etc.

In the treatment methods disclosed in these documents, the water in the cellular structures of cut flowers, i.e., the tissue water is removed and substituted by permeating polyethylene glycol, with dyeing as required, and as shown in FIG. 5, cut flowers are treated generally through a dehydration process, permeation process and drying process in this order, to obtain cut flowers as products appearing like natural flowers.

The dehydration process is effected while the cut flowers are fixed in a container having a proper amount of a molecular sieve spread over its bottom and filled with a solvent having a specific gravity smaller than that of water, for example, an anhydrous organic solvent such as acetone.

In the dehydration process, the water in the tissue of cut flowers, i.e., tissue water is gradually dissolved into the solvent while the solvent migrates into the tissue. So, in the tissue of cut flowers, tissue water is removed and substituted by the solvent, while the mechanical structure of the tissue is maintained.

Then, the permeation process is effected while the cut flowers are fixed in a container filled with a permeating solution obtained by dissolving substitutive polyethylene glycol into acetone and a cellosolve. In this case, the polyethylene glycol used is a mixture consisting of polyethylene glycol compounds different in molecular weight suitable for the kind of cut flowers to be treated, In this case, if the permeating solution contains a coloring matter such as a textile dye for acrylic fibers, the coloring matter permeates the tissue of cut flowers together with polyethylene glycol for dyeing them. That is, the permeation process and the dyeing process take place simultaneously.

After lapse of a certain time in the permeation process, the permeating solution is discharged, and the cut flowers are taken out and dried in the subsequent drying process, to obtain cut flowers as products.

The prior art has the following problems.

A. Dehydration Process

The prior art has the following problem in the dehydration process.

As described above, since the water dissolved into the solvent from the tissue of cut flowers in the dehydration process is larger in specific gravity than the solvent, the specific gravity of acetone tends to gradually rise due to the dissolved water.

While the molecular sieve remains new, most of the dissolved water is adsorbed by the molecular sieve. So, the dehydration by the solvent continues without causing the specific gravity of the solvent affected by the dissolved water to rise greatly.

However, if the total amount of dissolved water exceeds the water adsorbability of the molecular sieve with the progression of the dehydration process, the water remaining without being adsorbed raises the specific gravity of the solvent sharply, to quickly deprive the solvent of its adsorbability.

Since the prior art does not monitor the change of dehydratability, the dehydration process may be continued to waste time even though the dehydratability of the solvent is lost. Thus, efficient dehydration is difficult.

B. Drying Process

The prior art has the following problem since the cut flowers delivered from the permeation process are dried into products without being washed.

Since the acetone and cellosolve in the permeating solution are volatile, they are diffused into air in the drying process, but polyethylene glycol as a high molecular material remains deposited on the outside surfaces of petals.

The polyethylene glycol remaining deposited on the outside surfaces of petals like this absorbs water in air if the humidity is higher than a certain level, and becomes sticky to touch. So, the phenomenon remarkably lowers the commercial value of cut flowers.

C. Dyeing Process

In the prior art, depending on the kinds of cut flowers, uneven dyeing can happen without allowing even dyeing, to remarkably lower the commercial value of cut flowers.

The inventor intensively experimentally studied and found that the uneven dyeing is caused because the permeation of the permeating solution into the cellular structures of petals occurs differently from portion to portion in the petals.

In the prior art, the water in the cellular structures is substituted by an anhydrous organic solvent such as acetone in the dehydration process, and the solvent is substituted by the permeating solution containing polyethylene glycol in the permeation process. In this case, the substitution rate is different from cellular structure to cellular structure.

Therefore, after lapse of a certain time in the permeation process, the solvent is filly substituted by the permeating solution in the cellular structures higher in substitution rate, to dye the cellular structures by the coloring matter contained in the solvent, but in the cellular structures lower in substitution rate, the solvent is less substituted by the permeating solution, to keep the color remaining diluted.

D. Permeating Solution, etc.

In the prior art, when the cut flowers to be treated include plural colors and are intended to be treated simultaneously, permeating solutions as many as the number of colors are necessary since each permeating solution contains one coloring matter for each color of flowers, and they occupy a vast space.

Furthermore, if the permeating solution for any disused color is dumped, such problems as waste treatment and resource wastage arise because of the organic solvent contained, and if the permeating solution is stored as contained in a container, it needs an extra storage space.

SUMMARY OF THE INVENTION

An object of the present invention is to solve the problem described in the above A, and the object can be achieved by a treatment method for preserving cut flowers, which has a dehydration process for removing the tissue water of cut flowers using a solvent, and a permeation process for letting polyethylene glycol permeate after dehydration, to substitute the solvent by polyethylene glycol, characterized in that the dehydration process is effected while cut flowers are fixed in a container having a proper amount of a molecular sieve spread over its bottom and filled with a solvent having a specific gravity smaller than that of water, wherein the specific gravity of the solvent is measured to monitor the dehydratability with the progression of dehydration, for detecting the time for exchanging the molecular sieve.

According to this method, the change in the dehydratability of the solvent can be monitored by measuring the specific gravity of the solvent, and the time when the specific gravity sharply rises is detected as the time for exchanging the molecular sieve for a new one, to restore the dehydratability of the solvent, thereby allowing the solvent to be continuously used and allowing the dehydration process to be continued without waste of time.

The molecular sieve removed from the container for exchange can be dried for re-use.

Another object of the present invention is to solve the problem described in the above B, and the object can be achieved by a treatment method for preserving cut flowers, which has a dehydration process for removing the tissue water of cut flowers using a solvent, and a permeation process for letting polyethylene glycol permeate after dehydration, to substitute the solvent by polyethylene glycol, characterized in that the permeation process is effected by a solution obtained by dissolving polyethylene glycol into a solvent, wherein a washing process for washing the cut flowers containing polyethylene glycol as a substitute of tissue water by a solvent not containing polyethylene glycol is added.

According to this method, the polyethylene glycol remaining deposited on the outside surfaces of petals after the permeation process can be washed away by a solvent, and the stickiness otherwise caused after the drying process can be prevented by removing the extra polyethylene glycol deposited on the outside surfaces of petals.

A further other object of the present invention is to solve the problem described in the above C, and the object can be achieved by adding a coloring matter for dyeing to the permeating solution used in the permeation process and also to the dehydrating solvent used in the dehydration process in the above method.

According to this method, a coloring matter is contained in the solvent occupying the cellular structures as a substitute of tissue water as achieved in the dehydration process. So, when a coloring matter is added for dyeing in the permeation process, even the portions of petals low in the rate of substituting the solvent by the permeating solution have the same coloring matter concentration, and uneven dyeing can be avoided.

A still further other object of the present invention is to solve the problem described in the above D, and the object can be achieved by having a decoloration process for letting the permeating solution, dehydrating solution or washing solution respectively containing a coloring matter pass through a column packed with a decoloring agent, so that the permeating solution, dehydrating solution or washing solution delivered from the decoloration process may be re-used.

According to the above method, since the permeating solution, dehydrating solvent or washing solvent respectively containing a coloring matter for dyeing can be re-used after decoloration, it is not necessary to dump the permeating solution, dehydrating solvent or washing solvent of any disused color. So, such problems as waste treatment and resource wastage do not arise, and the storage space for them is not required.

In the present invention, the cut flowers to be treated for preservation also include leaves and stems.

BRIEF DESCRIPTION OF THE DRAWINGS

FIG. 2 is a process flow chart as a second embodiment of the treatment method for preserving cut flowers of the present invention.

DETAILED DESCRIPTION OF THE PREFERRED EMBODIMENTS

Preferred embodiments of the present invention are described below in more detail in reference to the attached drawings.

Embodiment 1

Figure 1:
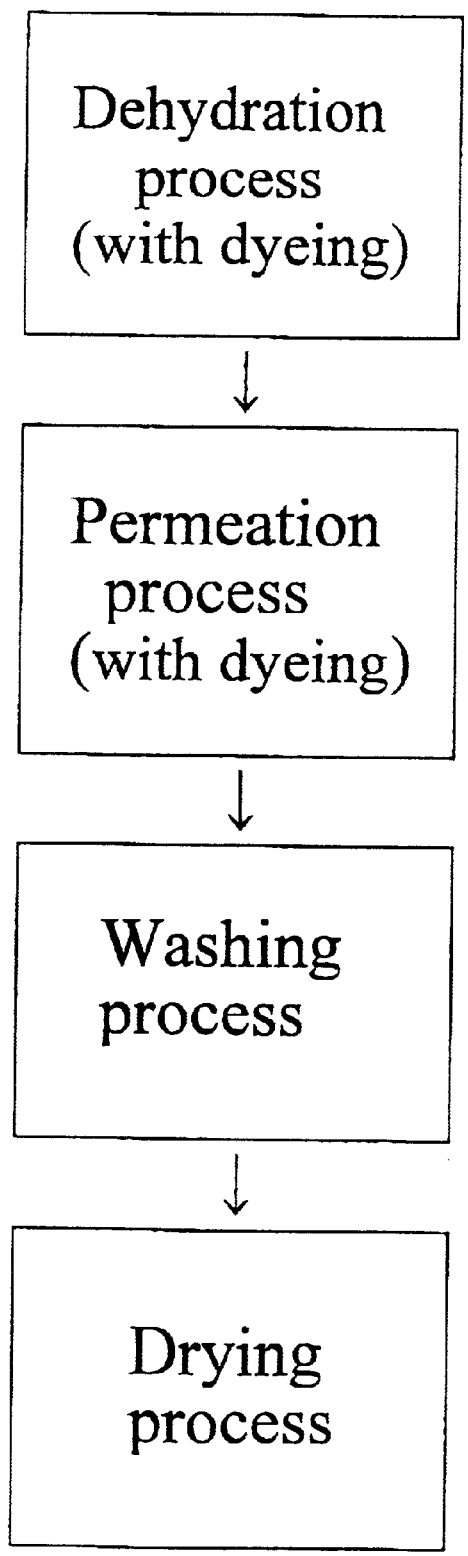
FIG. 1 is a process flow chart as a first embodiment of the treatment method for preserving cut flowers of the present invention.

FIG. 1 is a process flow chart as embodiment 1 of the treatment method for preserving cut flowers of the present invention. The embodiment 1 has a dehydration process, permeation process, washing process and drying process, and in the dehydration process and the permeation process, a coloring matter for dyeing is added. That is, the dyeing process takes place concurrently with the dehydration process and the permeation process.

a. Dehydration Process

At first in the dehydration process, as in the above prior art, a molecular sieve (zeolite) for adsorbing the water dissolved from petals was spread with a thickness of about 2 cm over the bottom of a dehydration container with a proper size, i.e., with a size suitable for the quantity of the cut flowers to be treated simultaneously, and the cut flowers were fixed in the dehydration container by proper supports. The container was filled with a solvent having a specific gravity smaller than that of water, for example, 100% acetone as a solvent for dehydration treatment.

In this case, in the present invention, a coloring matter for desired dyeing was added to the dehydrating solvent. The added coloring matter and the concentration are described later, since they were the same as those used in the permeation process described later.

In this state, the dehydration process was effected at room temperature (20~30° C.), and by treatment for at least 24 hours, dehydration could be achieved. Even if the dehydration process was effected for 48 hours, no special advantage was found.

During the dehydration process, the specific gravity of the solvent was incessantly measured by a specific gravity meter, to be monitored.

In an experiment, during the dehydration process, the specific gravity of the solvent, 100% acetone, gradually increased from 0.78, but after it exceeded 0.82, it rose sharply. At a specific gravity of 0.85, the effect of dehydration was little observed.

From the above, it can be estimated that under the experimental conditions, the total quantity of dissolved water exceeded the water adsorbability of the molecular sieve about the time when the specific gravity of the solvent became 0.82.

Therefore, if the molecular sieve is exchanged for a new one, the dehydratability of the solvent can be restored and the solvent can be used continuously. So, without waste of time, the dehydration process can proceed. The molecular sieve removed from the container for exchange can be dried for re-use.

In the above dehydration process, the water in the cellular structures of cut flowers, i.e., tissue water was gradually dissolved out into acetone, while acetone migrated into the tissue together with the coloring matter dissolved in it. So, while the mechanical structure of the cut flowers was maintained, the tissue water was gradually substituted by acetone, to be removed. Since the acetone occupying the tissue of the cut flowers, to substitute the tissue water contained the coloring matter at a predetermined concentration, the cellular structures were dyed by the coloring matter.

b. Permeation Process

Then, in the permeation process, a permeating solution obtained by dissolving substitutive polyethylene glycol into acetone and a cellosolve was supplied into a permeation container having cut flowers fixed in it.

The permeating solution was prepared by mixing polyethylene glycol compounds different in molecular weight (e.g., PEG 1000 and PEG 400) at a proper ratio, for example, at the following ratio, dissolving the mixture into a mixed solvent consisting of acetone: a cellosolve=1:1, etc., and adding the same coloring matter as used in the dehydration process to the solution at a predetermined concentration.

Example of permeating solution

PEG 1000 500 g
PEG 400 100 ml

A mixed solvent consisting of acetone:a cellosolve=1:1 is added to make one liter as the total amount.

The permeating solution in this composition ratio is solidified at 15° C. or lower. So it was kept at a treatment temperature higher than the solidification temperature, for example, about 25~35° C. on a hot water bath or in an incubator, etc. for treatment for about 24 hours, to achieve the optimum permeation effect.

Theoretically, permeation treatment at a higher temperature is expected to be completed in a shorter time, but in an actual experiment, polyethylene glycol could permeate more evenly by treatment at room temperature (20~30° C.) for 24 hours than by treatment at 50° C. for 12 hours.

Examples of coloring matters to be added in the dehydration process and the permeation process:

| Example 1 | Coloring matter | Methyl Red |
|---|---|---|
| | Color | Vermilion |
| | Concentration | 3 (g/l) |
| Example 2 | Coloring matter | Tartrazine |
| | Color | Yellow |
| | Concentration | 1 (g/l) |
| Example 3 | Coloring matter | Acid Green 25 |
| | Color | Green |
| | Concentration | 2 (g/l) |
| Example 4 | Coloring matter | Acid Blue 80 |
| | Color | Blue |
| | Concentration | 2 (g/l) |

The above coloring matters are solids (powders), and each concentration is based on the amount of the dehydrating solvent or the permeating solution.

For dyeing cut flowers in primary colors, the above coloring matters are used respectively singly, but for dyeing in any intermediate color, these coloring matters can be mixed adequately.

In the above permeation process, the acetone substituting the tissue water in the cellular structures is substituted by the permeating solution containing polyethylene glycol, and the permeating rate is different from cellular structure to cellular structure. That is, in the cellular structures higher in substitution rate, acetone is soon replaced by the permeating solution, but in the cellular structures lower in substitution rate, acetone remains in the cellular structures without being replaced by the permeating solution unless a sufficient time elapses.

For this reason, in the prior art in which a coloring matter is added only to the permeating solution for dyeing only in the permeation process, unless a sufficient time is taken to allow acetone to be replaced by the permeating solution in all the cellular structures, the quantity of the coloring matter migrating into the cellular structures lower in substitution rate becomes smaller in inverse proportion to the amount of remaining acetone. So, the coloring matter concentration of the cellular structures remains low, keeping the color of the cellular structures remaining diluted, to cause uneven dyeing.

In other words, the reason why uneven dyeing occurs in the prior art is that the permeation of the permeating solution into the cellular structures occurs differently from portion to portion, that is, the amount of permeating polyethylene glycol is different from petal portion to petal portion in the cut flowers.

On the contrary, in the embodiment 1, since the coloring matter is added also for dehydrating acetone, the acetone substituting the tissue water in the cell structures also contains the coloring matter, and even if acetone remains in the cellular structures lower in substitution rate, the coloring matter concentration in the cell tissue remains unchanged, allowing uneven dyeing to be avoided.

However, though the present invention in which the coloring matter is added in the dehydration process can avoid uneven dyeing, the substitution rate different from cellular structure to cellar structure cannot be raised. So, the treatment time in the permeation process must be decided considering undesirable effects such as the strain of cut flowers and partial excessive drying caused by different amounts of permeating polyethylene glycol, in relation with the productivity of cut flowers to be dyed.

That is, in general, when unevenly dyed products are compared with evenly dyed products rather uneven in the permeating amount of polyethylene glycol, the unevenly dyed products are evaluated very low. Therefore if the effect due to some unevenness in the quantity of polyethylene glycol is practically negligible, the embodiment 1 has an advantage that the productivity does not decline since the uneven dyeing can be avoided without extending the treatment time in the permeation process.

It is suitable that the coloring matter concentration in the dehydration process is equal to or rather lower than the coloring matter concentration in the permeation process.

c. Washing Process

In the washing process, the cut flowers delivered from the permeation process were immersed for washing in a mixed solvent of acetone: a cellosolve=1:1 for a predetermined time, say, 2 to 8 hours.

In this case, if the cut flowers are immersed in the solvent for a period of time longer than necessary, the polyethylene glycol contained in the cellular structures of petals in the permeation process also comes out. So, time control is necessary. The immersion time can be set based on the data obtained by a preliminary experiment performed for the kind, size, etc. of the cut flowers.

d. Drying Process

After the washing process, the cut flowers are dried in any adequate drying process as described in the above prior art, to obtain cut flower products which can remain appearing like natural flowers for a long time for decoration.

Embodiment 2

FIG. 2 is a process flow chart as embodiment 2 of the treatment method for preserving cut flowers of the present invention. In this embodiment 2, the treatment processes include a dehydration process, permeation process, washing process and drying process as in the embodiment 1, but in the embodiment 2, no coloring matter is added to the dehydrating solvent in the dehydration process unlike the embodiment 1 Since the other processes are the same as those of the embodiment 1, double explanation is avoided here.

The embodiment 2 is suitable for the cut flowers which are less uneven in the permeation of the permeating solution into the cellular structures.

The embodiment 2 has an advantage that since the container for dehydration is not affected by the coloring matter for dyeing in the permeation process, a common container can be used for dehydration, though the embodiment 1 requires dehydration containers as many as coloring matters used for dyeing.

Embodiment 3

Figure 3:
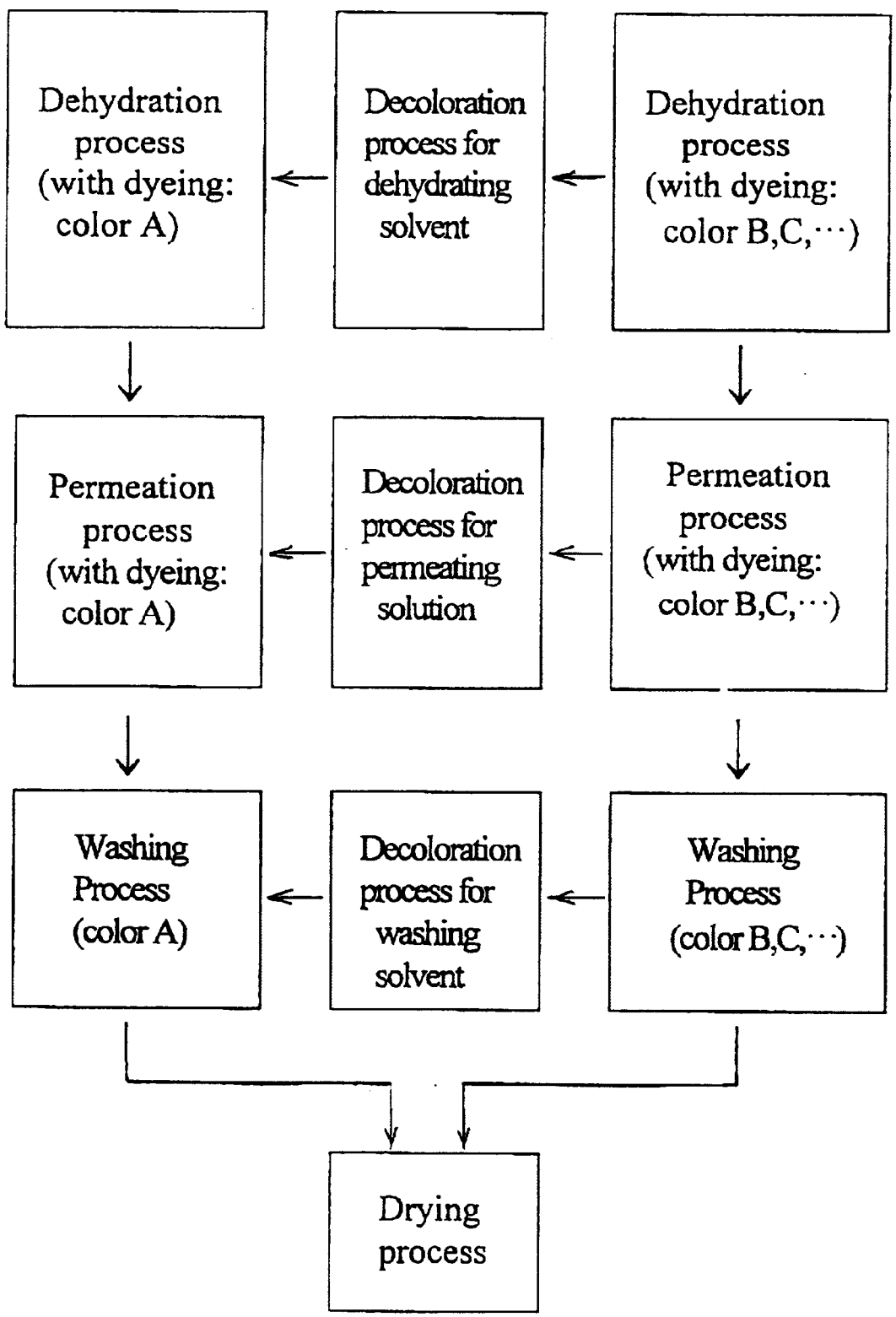
FIG. 3 is a process flow chart as a third embodiment of the treatment method for preserving cut flowers of the present invention.

FIG. 3 is a process flow chart as embodiment 3 of the treatment method for preserving cut flowers of the present invention. In the embodiment 3, cut flowers are treated by a dehydration process, permeation process, washing process and drying process, to be preserved. In this case, in the dehydration process and the permeation process, they are dyed in desired colors (A, B, C, . . . ). This embodiment 3 handles plural colors (A, B, C, . . . ), but is the same as the embodiment 1 in the treatment flow for each color.

If cut flowers of plural colors are treated in this embodiment 3 simultaneously, the dehydrating solutions, permeating solutions and washing solutions respectively containing a coloring matter of any of the colors must be contained in the dehydration containers, permeation containers and washing containers provided as many as the respective coloring matters for the respective colors.

While cut flower products of various colors are produced like this, if the production of cut flowers of any specific color becomes unnecessary, the dehydrating solution, permeating solution and washing solution of the color are not dumped, but are decolored in a decoloration process.

That is, the dehydrating solution, permeating solution and washing solution are fed through respective columns packed with a decoloring agent, to be decolored, in the decoloration process, and after decoloration, they are re-used in the respective treatment processes of any one of the colors of cut flowers being still produced.

For example, in FIG. 3, the dehydrating solvent, permeating solution and washing solvent of the disused color among colors (B, C, . . . ) can be re-used for color A in the dehydration process, permeation process and washing process. Of course, the re-use between any other colors is allowed.

Thus, in the embodiment 3, such problems as waste treatment and resource wastage do not arise, and the dehydrating solvent, permeating solution and washing solvent can be effectively utilized.

Since all the coloring matters as described above have benzene rings, active carbon can be used as a decoloring agent for achieving substantially perfect decoloration, to allow re-use of the solutions in the respective processes for any other color.

Embodiment 4

Figure 4:
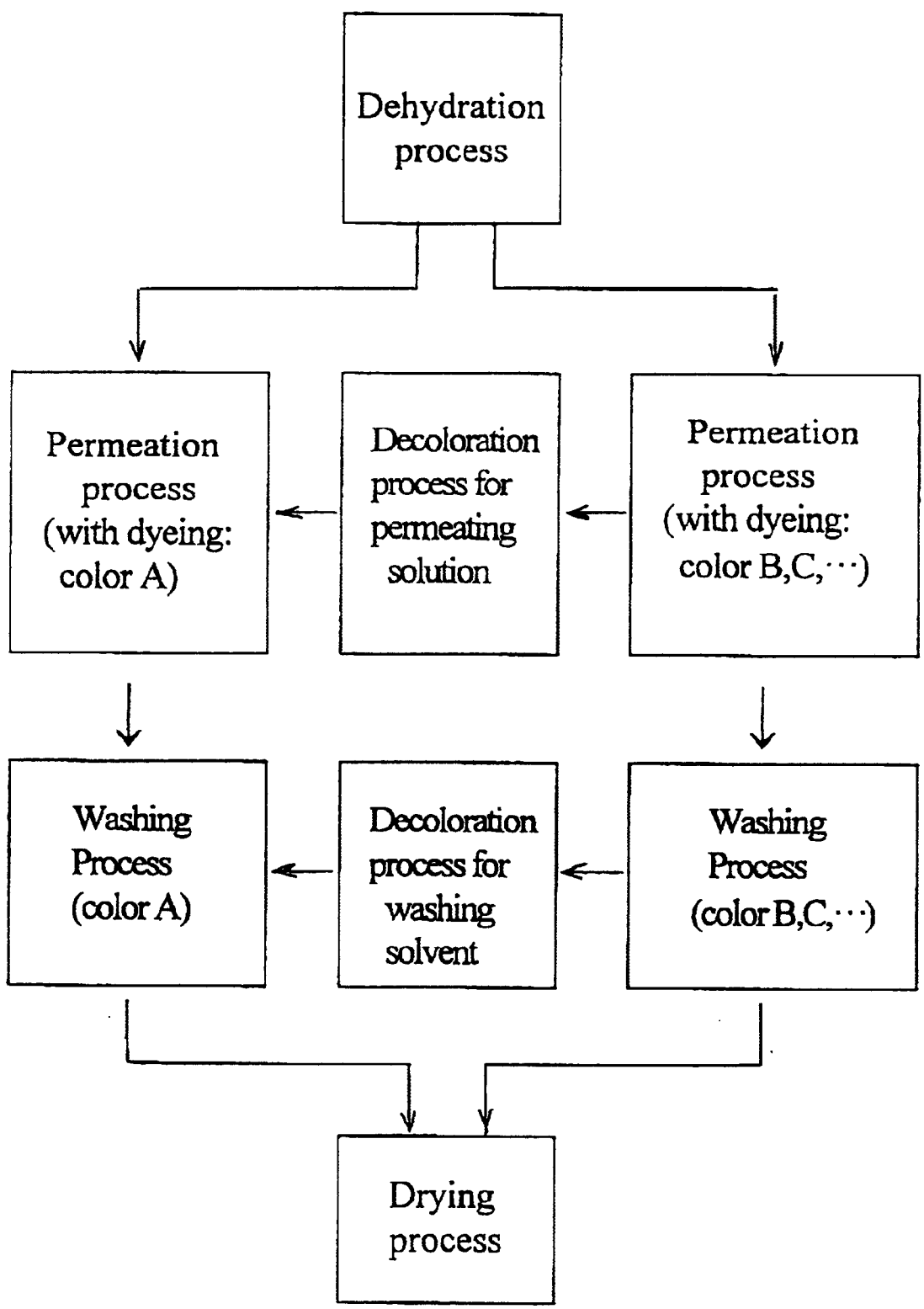
FIG. 4 is a process flow chart as a fourth embodiment of the treatment method for preserving cut flowers of the present invention.
Figure 5:
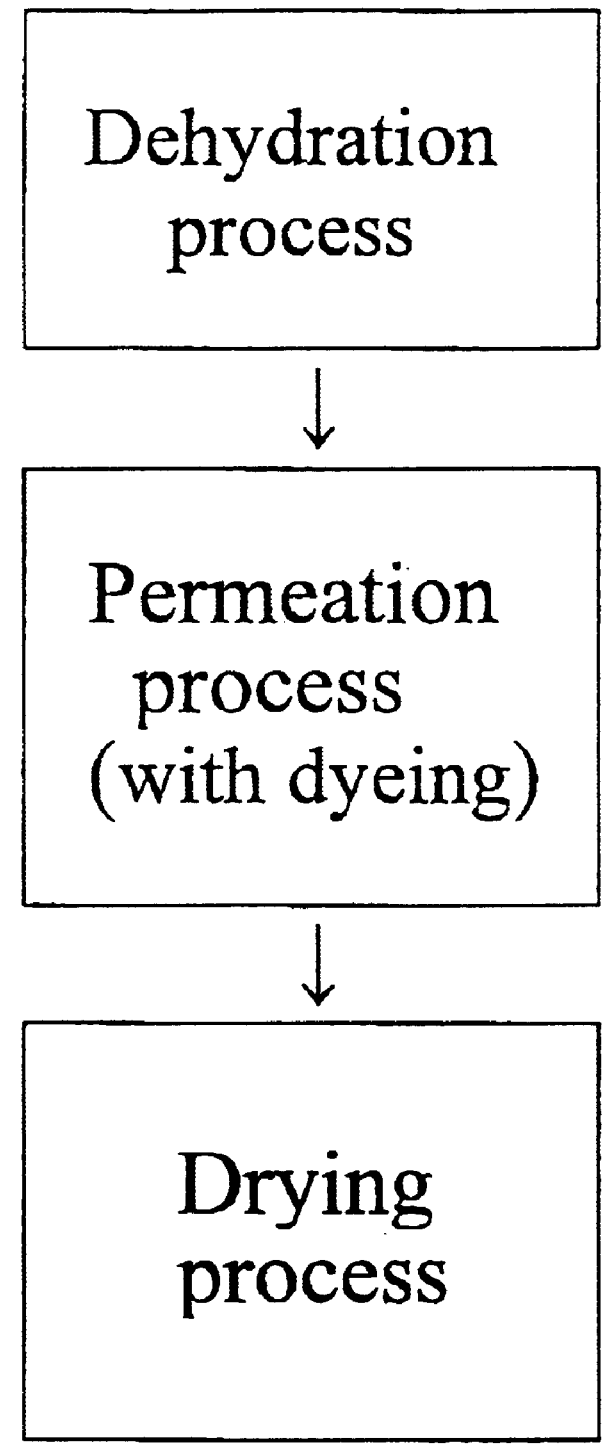
FIG. 5 is a process flow chart of the treatment method for preserving cut flowers as the prior art.

FIG. 4 is a process flow chart as embodiment 4 of the treatment method for preserving cut flowers of the present invention. This embodiment 4 has the dehydration process, permeation process, washing process and drying process for respective colors of cut flowers like the embodiment 3, but does not have any coloring matter added to the dehydrating solvent in the dehydration process. Since the other processes are the same as those in the embodiment 3, double explanation is avoided here.

This embodiment is suitable for the cut flowers which are less uneven in the permeation of the permeating solution into the cellular structures, like the embodiment 2.

That is, the embodiment 4 has an advantage that since the container for dehydration is not affected by the coloring matter for dyeing in the permeation process, a common container can be used for dehydration, though the embodiment 3 requires dehydration containers as many as coloring matters used for dyeing.

Therefore, in this embodiment, as illustrated, the permeating solutions and the washing solutions are decolored in the decoloration process, to be re-used.

Embodiment 5

In embodiment 5, the coloring matter used for dyeing in the embodiments 1 to 4 is a coloring matter which develops different colors depending on whether it is exposed to natural light and ordinary artificial light or to ultraviolet rays, as shown in the following examples.

| Example 1 | Coloring matter | Yellow No. 4 food dye, tartrazine |
|---|---|---|
| | Colors | Natural light and ordinary artificial light: Yellow |
| | | Ultraviolet rays: Orange |
| | Concentration | 1 (g/l) |

This coloring matter is a solid (powder), and the concentration is based on the amount of the dehydrating solvent or the permeating solution.

| Example 2 | Coloring matter | Red No. 104 food dye, Acid Red 92 |
|---|---|---|
| | Colors | Natural light and ordinary artificial light: Red |
| | | Ultraviolet rays: Greenish yellow |
| Example 3 | Coloring matter | Red No. 106 food dye, Acid Red 52 |
| | Colors | Natural light and ordinary artificial light: Bluish red |
| | | Ultraviolet rays: Light yellow |

The above Examples 1 to 3 use food dyes, and in addition, other food dyes such as Acid Green 25 and Acid Blue 80 can also be used. Their concentrations can be set adequately.

These coloring matters are respectively singly used for dyeing cut flowers in primary colors, but can be adequately mixed for dyeing in intermediate colors.

The above coloring matters develop different colors depending on whether they are exposed to natural light and ordinary artificial light or to ultraviolet rays. These coloring matters can be selected from food dyes as described above. However, in the present invention, coloring matters obtained by adding a fluorescent material to coloring matters without having such a nature can also be used.

For example, a coloring matter obtained by mixing a fluorescent material such as fluorescein or rhodamine used for fluorescent dyes, etc. to an ordinary coloring matter such as Methyl Red (color: vermilion) can also be used.

The cut flowers produced according to the embodiment 5 can develop a color of petals different from that in the daytime, by irradiating them with ultraviolet rays such as a black light at night, and an outstanding decorative effect which cannot be achieved with natural flowers can be obtained.

Industrial Applicability

The present invention as described above can provide the following advantages by applying the above respective embodiments.

a. In the dehydration process, it can be avoided that the dehydration process is kept proceeding even though the dehydratability of the solvent is lost. Therefore, the dehydration process can be kept proceeding efficiently without waste of time.

b. The polyethylene glycol remaining deposited on the outside surfaces of petals after the permeation process can be washed away by a solvent, and since the stickiness otherwise caused after the drying process can be prevented by removing the extra polyethylene glycol remaining on the outside surfaces of petals, the commercial value of the products can be significantly raised.

c. Uneven dyeing can be avoided without extending the treatment time in the permeation process, hence without lowering the productivity.

d. Since the permeating solution, dehydrating solvent and washing solvent respectively containing a coloring matter for dyeing are decolored, to be re-used, it is not necessary to dump the permeating solution, dehydrating solvent or washing solvent of any disused color. So, such problems as waste treatment and resource wastage can be avoided, and the extra storage space for them is not required.

e. The cut flowers treated to be preserved can develop a color different from that developed in the daytime, by exposing them to ultraviolet rays such as a black light at night and an outstanding decorative effect which cannot be achieved with natural flowers can be achieved.

What is claimed is:

1. In a treatment method for preserving cut flowers, which includes a dehydration process for removing tissue water of cut flowers using a solvent, and a permeation process in which polyethylene glycol permeates said flowers after dehydration, whereby to substitute polyethylene glycol for the solvent in the cut flowers, and wherein the dehydration process is effected while the cut flowers are held in a container having therein a proper quantity of molecular sieve for adsorption of water, said container also having therein a solvent with a specific gravity smaller than that of water, the improvement comprising:
   (a) monitoring the change of dehydratability of said solvent during the progression of dehydration by incessantly measuring the specific gravity of the solvent, for detecting the time for exchanging the molecular sieve, and
   (b) replacing said molecular sieve with a fresh molecular sieve substantially free of water when the total quantity of dissolved water in the solvent as determined by the specific gravity measurements exceed the water adsorbability of the molecular sieve.

2. The treatment method for preserving cut flowers, according to claim 1, wherein acetone is used as the solvent in the dehydration process.

3. The treatment method for preserving cut flowers, according to claim 1, wherein a mixed solvent consisting of acetone and cellosolve is used as a solvent in the permeation process.

4. The treatment method for preserving cut flowers, according to claim 1, further comprising adding to the permeating solution in the permeation process coloring matter for dyeing.

5. The treatment method for preserving cut flowers, according to claim 4, wherein coloring matter is added which develops different colors depending whether it is exposed to natural light and ordinary artificial light or to ultraviolet rays.

6. The treatment method for preserving cut flowers, according to claim 5, wherein said coloring matter develops different colors depending upon whether it is exposed to natural light and ordinary artificial light or to ultraviolet rays.

7. The treatment method for preserving cut flowers, according to claim 5, wherein said coloring matter is a food dye.

8. The treatment method for preserving cut flowers, according to claim 5, further comprising mixing a fluorescent material to produce said coloring matter.

9. The treatment method for preserving cut flowers, according to claim 4, further comprising passing through a column packed with a decoloring agent the permeating solution containing a coloring matter, thereby decoloring the permeating solution for reuse.

10. The treatment method for preserving cut flowers, according to claim 9, wherein the decoloring agent is active carbon.

11. The treatment method for perserving cut flowers, according to claim 1, further comprising adding coloring matter for dyeing to both the permeating solution in the permeation process and to the dehydrating solvent in the dehydration process.

12. The treatment method for preserving cut flowers, according to claim 11, further comprising passing through a column packed with a decoloring agent the dehydrating solvent containing coloring matter thereby decoloring the dehydrating solvent for reuse.

13. The treatment method for preserving cut flowers, according to claim 12, wherein the decoloring agent is active carbon.

14. A treatment method for preserving cut flowers, according to claim 11, wherein coloring matter is added which develops different colors depending upon whether it is exposed to natural light and ordinary artificial light or to ultraviolet rays.

15. The treatment method for preserving cut flowers, according to claim 11, further comprising passing through a column packed with a decoloring agent the permeating solution containing a coloring matter thereby decoloring the permeating solution for reuse.

16. In a treatment method for preserving cut flowers which includes a dehydration process for removing the tissue water of cut flowers using a first solvent, and a permeation process in which polyethylene glycol permeates said flowers after dehydration, whereby to substitute polyethylene glycol for the first solvent in the cut flowers and wherein the permeation process is effected by a solution obtained by dissolving polyethylene glycol in a second solvent, the improvement comprising the step of:
   (a) washing the cut flowers containing polyethylene glycol as a substitute for tissue water with the second solvent free of polyethylene glycol to wash away any polyethylene glycol remaining on outer surfaces of petals of the cut flowers.

17. The treatment method for perserving cut flowers, according to claim 16, wherein a mixed solvent consisting of acetone and cellosolve is used as the second solvent in the washing process.

18. The treatment method for preserving cut flowers, according to claim 16, further comprising adding to the permeating solution in the permeation process after dehydrating coloring matter for dyeing, and feeding the washing solvent through a column packed with a decoloring agent, for decoloring the washing solvent for reuse.

19. The treatment method for preserving cut flowers, according to claim 18, wherein the decoloring agent is active carbon.

20. The treatment method for perserving cut flowers, according to claim 16, further comprising adding coloring matter for dyeing to the first dehydration solvent in the dehydration process and to the second permeating solution in the permeation process, and feeding the washing solvent through a column packed with a decoloring agent, for decoloring the washing solvent for reuse.

21. The treatment method for preserving cut flowers, according to claim 20, wherein the decoloring agent is active carbon.

22. The treatment method for preserving cut flowers, according to claim 16, wherein acetone is used as the first solvent in the dehydration process.

23. The treatment method for preserving cut flowers, according to claim 16, wherein a mixed solvent consisting of acetone and a cellosolve is used as the second solvent in the permeation process.

24. The treatment method for preserving cut flowers, according to claim 16, further comprising adding coloring matter for dyeing both to the permeating solution used in the permeation process and to the dehydrating first solvent used in the dehydration process.

* * * * *